US006165465A

United States Patent [19]
Wang et al.

[11] Patent Number: 6,165,465
[45] Date of Patent: *Dec. 26, 2000

[54] IMMUNOLOGIC ENHANCEMENT OF THE SOMATOGENIC EFFECT OF SOMATOTROPIN WITH AN ANTIBODY

[75] Inventors: Bosco Shang Wang, Cranbury; Araceli L. Lumanglas, Jersey City; Ian C. Hart, Pennington, all of N.J.

[73] Assignee: American Cyanamid Company, Madison, N.J.

[*] Notice: This patent is subject to a terminal disclaimer.

[21] Appl. No.: 07/521,695

[22] Filed: May 15, 1990

[51] Int. Cl.[7] ................. A61K 39/395; G01N 33/563; C07K 1/00; C12P 21/08
[52] U.S. Cl. ................. 424/145.1; 424/139.1; 424/141.1; 436/513; 436/536; 530/386; 530/387.1; 530/388.1; 530/388.24
[58] Field of Search ................. 424/85.8, 139.1, 424/141.1, 145.1; 530/387, 388.24, 386, 387.1, 388.1; 436/513, 536

[56] References Cited

U.S. PATENT DOCUMENTS

| 4,599,229 | 7/1986 | Maccecchini ................. 424/85 |
| 4,837,202 | 6/1989 | Edwards et al. ............... 514/12 |
| 4,925,922 | 5/1990 | Byers et al. ................... 530/391 |

FOREIGN PATENT DOCUMENTS

| 104920 | 4/1984 | European Pat. Off. ........ C12N 15/00 |
| 111389 | 6/1984 | European Pat. Off. ........ C12N 15/00 |
| 137234 | 4/1985 | European Pat. Off. ........ A61K 39/395 |
| 284406 | 9/1988 | European Pat. Off. ........ C07K 7/08 |
| 303972 | 2/1989 | European Pat. Off. ........ C12N 15/00 |
| WO 89/00166 | 1/1989 | WIPO ............................. C07K 7/06 |
| WO 89/01490 | 2/1989 | WIPO ............................. C07K 7/00 |

OTHER PUBLICATIONS

Wang, B.S., et al., J. Endocrinology, "Potentiation of the Growth–Promoting Activity of Porcine Growth Hormone (pGH) with an Antibody Generated in Rabbits to the Peptide Sequence pGH110–118", 127:481–485, 1990.
Abdel–Meguid, S.S., et al., Proc. Natl. Acad. Sci., 84, 6434–6437, (1987).
Groesbeck, M.D., and Parlow, A.F., Endocrinology, 120, 2582–2590, (1987).
Aston, R., et al., Molecular Immunology, 24, 143–150 (1987).
Ferrara, P., et al., European J. Immunology, 9, 1020–1023 (1979).
Pena, C., et al., Molecular Immunology, 17, 1487–1491 (1980).
Retegui, L.A., et al., Endocrinology, 111, 668–676 (1982).
Hughes, J.P., and Friesen, H.G., Ann. Rev. Physiol., 47, 469–482 (1985).
Arthur C. Guyton, M.D., Textbook of Medical Physiology, Pub. W.B.Saunders Co., 1981, pp. 919–923.

*Primary Examiner*—Rodney P. Swart
*Attorney, Agent, or Firm*—Barbara L. Renda

[57] ABSTRACT

The present invention is directed to antibodies, in particular monoclonal antibodies, of porcine somatotropin (pST). When these antibodies are administered together with pST, the growth of vertebrates is greater than that achieved with the administration of pST alone. The invention is also directed to an increase in the growth of vertebrates which persists over long periods when an antibody to a somatotropin is administered together with such somatotropin.

22 Claims, 7 Drawing Sheets

FIG. 7 ically significant results as follows: *=p<0.05;
IMMUNOLOGIC ENHANCEMENT OF THE SOMATOGENIC EFFECT OF SOMATOTROPIN WITH AN ANTIBODY

FIELD OF THE INVENTION

This invention relates to the preparation of antibodies, in particular monoclonal antibodies, to porcine somatotropin (pST). When these antibodies are administered together with pST, the growth of vertebrates is greater than that achieved with the administration of pST alone. This invention also relates to the general finding that the administration of antibodies to somatotropins of vertebrates, together with such somatotropins, results in an increase in growth of vertebrates which, as compared with the administration of such somatotropins alone, persists over prolonged periods.

BACKGROUND OF THE INVENTION

Somatotropin is a polypeptide secreted by the anterior pituitary in warm-blooded animals and acts through specific cell surface receptors located primarily in the liver (Hughes, J. P. and Friesen, H. G., Ann. Rev. Physiol., 47, 469–482 (1985)). Somatotropin is useful to enhance growth of such animals as bovine (cattle), porcine (pigs), caprine (goat), avian (chicken, turkey, geese, etc.) and rabbit, among others. Somatotropin is also useful to enhance the growth of other vertebrates, such as fish.

Specifically, the growth hormone pST is native to swine and accounts for maturation of the animal, including increasing the growth rate and the lean to fat ratio. It has been found that pST is a single chain polypeptide of 191 amino acids with two cystine bridges linking residues 53–164 and 181–189, respectively (Abdel-Meguid, S. S., et al., Proc. Nat. Acad. Sci., 84, 6434–6437 (1987).

Because endogenous amounts of pST are small, efforts have focused on the preparation of exogenous pST for use in large-scale agriculture. Efforts have also been directed to the identification of small portions of the pST molecule, the generation of antibodies to those portions, and the administration of those antibodies together with pST to enhance growth. See, for example, published European Patent Application 284,406.

SUMMARY OF THE INVENTION

Although the approaches described above have shown promise for enhancing animal growth, there is a continuing need to develop additional strategies and techniques in this area.

Accordingly, it is an object of this invention to develop antibodies, in particular monoclonal antibodies, to the entire pST molecule, as opposed to portions of that molecule.

It is a further object of this invention to improve growth by treating vertebrates with one or more such antibodies in combination with pST.

It is yet another object of this invention to achieve an equivalent potentiation of pST while reducing the amount of pST administered through the treatment of vertebrates with one or more such antibodies in combination with a reduced amount of pST.

It is still further object of this invention to accelerate the potentiation of pST by administering to vertebrates one or more such antibodies in combination with pST such that an equivalent potentiation is achieved with said combination in less time than that achieved with the administration of pST alone.

It is a more general object of this invention to potentiate the activity of a somatotropin over prolonged periods of time by administering to a vertebrate a somatotropin in combination with one or more antibodies to said somatotropin, such that the weight of the vertebrate continues to exceed that of a vertebrate treated with the same amount of the somatotropin alone over a given period of time.

The invention is also directed to antibodies of somatotropins having modified amino acid sequences, so long as the above-described growth enhancing functions of such antibodies are maintained.

These objects are accomplished in the description of the invention set forth below.

BRIEF DESCRIPTION OF THE FIGURES

In FIG. 1, several subsequent Figures and Table 1, monoclonal antibody is abbreviated as "MoAb".

DETAILED DESCRIPTION OF THE INVENTION

This invention is directed to the generation of antibodies, in particular monoclonal antibodies, to pST. Such antibodies are then administered together with pST to vertebrates, such as warm-blooded animals and fish, to enhance their growth performance by potentiating the activity of pST. Alternatively, these antibodies are administered to vertebrates which are thereafter treated with pST.

The monoclonal antibodies to pST of this invention affect the activity of pST in the following ways:

1) The antibodies potentiate the activity of pST when a vertebrate is administered an effective growth enhancing amount of pST and an effective pST-potentiating amount of one or more monoclonal antibodies to pST. Thus, over a given period of time with a given amount of pST, vertebrates also receiving such antibodies will exhibit increased growth.

2) The antibodies achieve an equivalent potentiation of pST while reducing the amount of pST administered when a vertebrate is administered an effective growth enhancing amount of pST and an effective pST-potentiating amount of one or more monoclonal antibodies to pST, such that an equivalent potentiation is achieved with said combination of pST and one or more monoclonal antibodies to pST as with a larger amount of pST administered alone. Thus, over a given period of time, the same growth is achieved with less pST if such antibodies are also administered.

3) The antibodies achieve an acceleration of the potentiation of pST when a vertebrate is administered an effective growth enhancing amount of pST and an effective pST-potentiating amount of one or more monoclonal antibodies of pST, such that an equivalent potentiation is achieved with said combination of pST and one or more monoclonal antibodies to pST in less time than with pST administered alone. Thus, for a given amount of pST the same growth is achieved in less time if such antibodies are also administered.

This invention is also directed to the more general observation that the improved growth resulting from the administration of antibodies to somatotropin (including, but not limited to pST) in combination with said somatotropin is not a transient phenomenon. Rather, vertebrate weights continue to exceed those of vertebrates treated with somatotropin alone over a given period of time. The antibodies potentiate the activity of a somatotropin over prolonged periods of time when a vertebrate is administered an effective growth enhancing amount of a somatotropin and an effective somatotropin-potentiating amount of one or more antibodies to said somatotropin, such that the weight of the vertebrate continues to exceed that of a vertebrate treated with the same amount of said somatotropin alone over a given period of time.

This invention is further directed to antibodies to peptides having amino acid sequences which are antigenically equivalent to that of a somatotropin. These peptides may be said to be antigenically equivalent to a somatotropin if their amino acid sequences differ by deletions from, additions to or substitutions to the somatotropin sequence, such that the secondary and/or tertiary configurations of the peptides are substantially unchanged from those of the somatotropin and antibodies can be generated to those peptides.

In one aspect of this invention, monoclonal antibodies are prepared by immunizing mice with a somatotropin, removing the spleens of the mice, preparing suspensions of lymphocytes, fusing these lymphocytes to mouse myeloma cells, culturing the cells and collecting supernatants of surviving hybridomas for antibody screening by solid-phase enzyme-linked immunosorbent assay (ELISA). Those hybridomas which produce desired antibodies are further subcloned and injected in mice. Ascites are then collected from the peritoneal cavities of mice and immunoglobulin (Ig) is purified by either ammonium sulfate precipitation or a protein A affinity column by fast protein liquid chromatography (FPLC). Samples of Ig so purified are assayed against antigens using ELISA to identify the antibodies formed.

In another aspect of this invention, polyclonal antibodies to a somatotropin are generated and purified from immunized warm-blooded animals such as swine and rabbits. Polyclonal antibodies are generated by immunizing vertebrates with such a somatotropin.

Polyclonal antibodies are recovered by first obtaining a blood sample from an immunized animal after a time sufficient from administration of the somatotropin for antibodies to be formed. The serum (which contains the antibodies) is isolated by conventional means such as centrifugation. Serum is separated into fractions containing Ig and lacking immunoglobulin (non-Ig) by means such as FPLC. Only the Ig fraction contains antibodies to the peptides. The antibodies are then isolated from the Ig fraction by sodium dodecyl sulfate-polyacrylamide gel electrophoresis (SDS-PAGE). The purity of the antibodies so isolated is greater than 98% as determined by SDS-PAGE. The antibody titer level is assayed using ELISA according to conventional procedures.

Although the somatotropin exemplified in this application is pST, a person skilled in the art may utilize the techniques described herein to generate monoclonal and polyclonal antibodies to other somatotropins.

The monoclonal and polyclonal antibodies of this invention may be used in two ways to potentiate and enhance the growth-promoting activity of a somatotropin. First, an antibody is administered to a vertebrate together with a somatotropin, such as pST. Alternatively, the vertebrate is treated with one or more doses of an anti-somatotropin antibody and is subsequently treated with somatotropin. In either procedure, more than one antibody to the particular somatotropin may be used. Thus, the invention also contemplates the administration of combinations of anti-somatotropin antibodies or their antigenic equivalents.

The antibodies may be administered by conventional routes such as subcutaneous injection, intramuscular injection and intravenous flow, as well as transdermal and oral administration. It is preferred to administer the antibodies in association with a suitable carrier. It is particularly preferred to use a dosage regimen where an initial administration of the antibodies is followed by one or more booster administrations of the same antibodies at regular time intervals.

The biological activity of these antibodies is tested in hypophysectomized (hypox) rats. Hypox-rats are growth-deficient as a result of surgical removal of their pituitary glands. Hypox-rats serve as a useful model for studying the effect of somatotropin on growth (Groesbeck, M. D. and Parlow, A. F., *Endocrinology*, 120, 2582–2590 (1987).

Treatment of these hypox-rats with a combination of pST and antibodies to pST enhances the growth-promoting effect of pST in the various manners described above. The pST used may be isolated from natural sources or may be prepared using recombinant techniques such as those described in published European patent applications 104, 920 or 111,389. The sources of and the method of isolation/ preparation of pST itself forms no part of this invention. The antibodies may also be used together with recombinant pST in which the amino acid sequence of native pST has been modified using a technique such as site-directed mutagenesis, so long as the growth enhancing function of pST is maintained. See, for example, co-pending, commonly-assigned U.S. Ser. No. 372,699, filed Jul. 3, 1989; see also published European patent application 303, 972.

Among the monoclonal antibodies being examined, the antibody PS-7.6 is found to possess particularly strong potentiation of pST activity and is chosen for further analysis. Monoclonal antibodies PS-3.12 and PS-8.3 are also found to give strong potentiation of pST activity.

Monoclonal antibody PS-7.6 is an $IgG_1$ subtype immunoglobulin with k light chain characteristics. An immunospecificity study (FIG. 1) indicates that it is highly reactive with pST, weakly with bST, but not with cST, PRL, SRIF or GRF.

Figure 2:
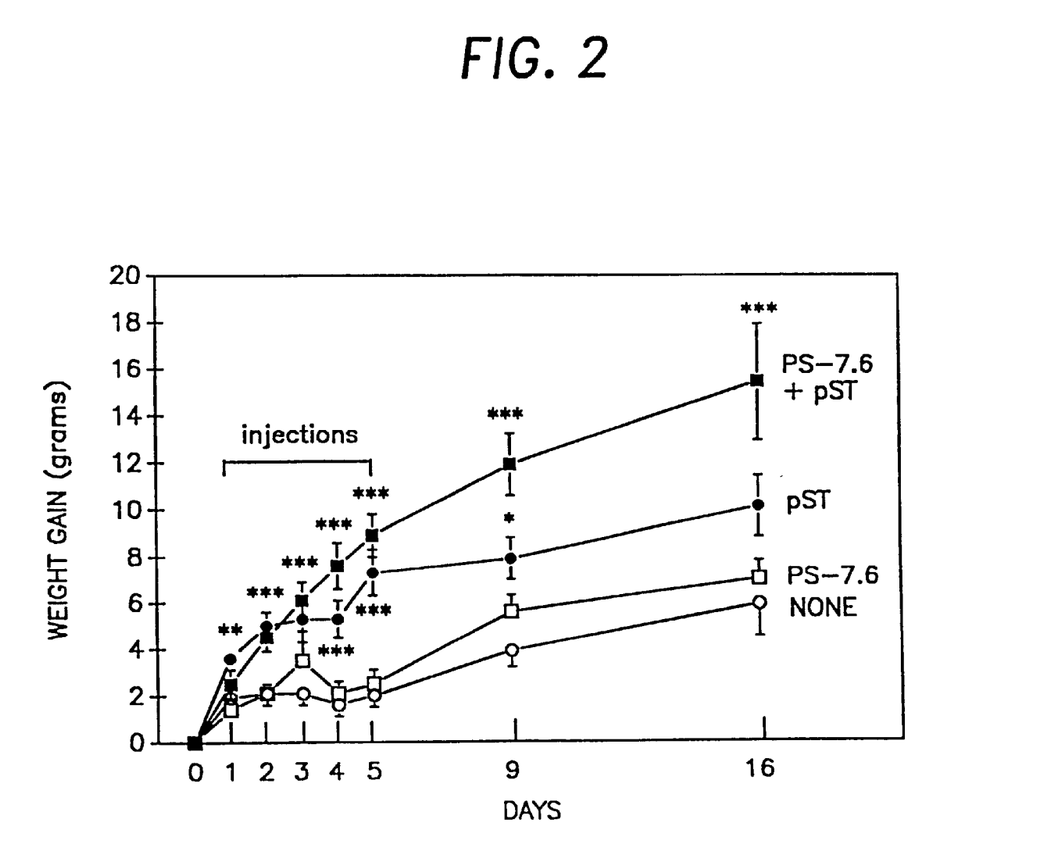
FIG. 2 depicts a time course study comparing the effect on the growth of hypophysectomized rats of treatment with pST alone, monoclonal antibody PS-7.6 alone, pST in combination with monoclonal antibody PS-7.6, or no treatment. The asterisks in this Figure, as well as FIGS. 3, 4 and 6, represent statistically significant results as follows: *=p<0.05; =p<0.01; *=p<0.001.

In a hypox-rat bioassay, it is demonstrated (FIG. 2) that injections with 5 µg of pST alone for five consecutive days stimulates the growth of these animals. This effect is significantly potentiated when pST is incubated with monoclonal antibody PS-7.6 for one hour at room temperature prior to administration. The growth profile of rats receiving monoclonal antibody PS-7.6 alone is similar to that of untreated controls, indicating that the antibody by itself is not a growth stimulant (FIG. 2).

Figure 3:
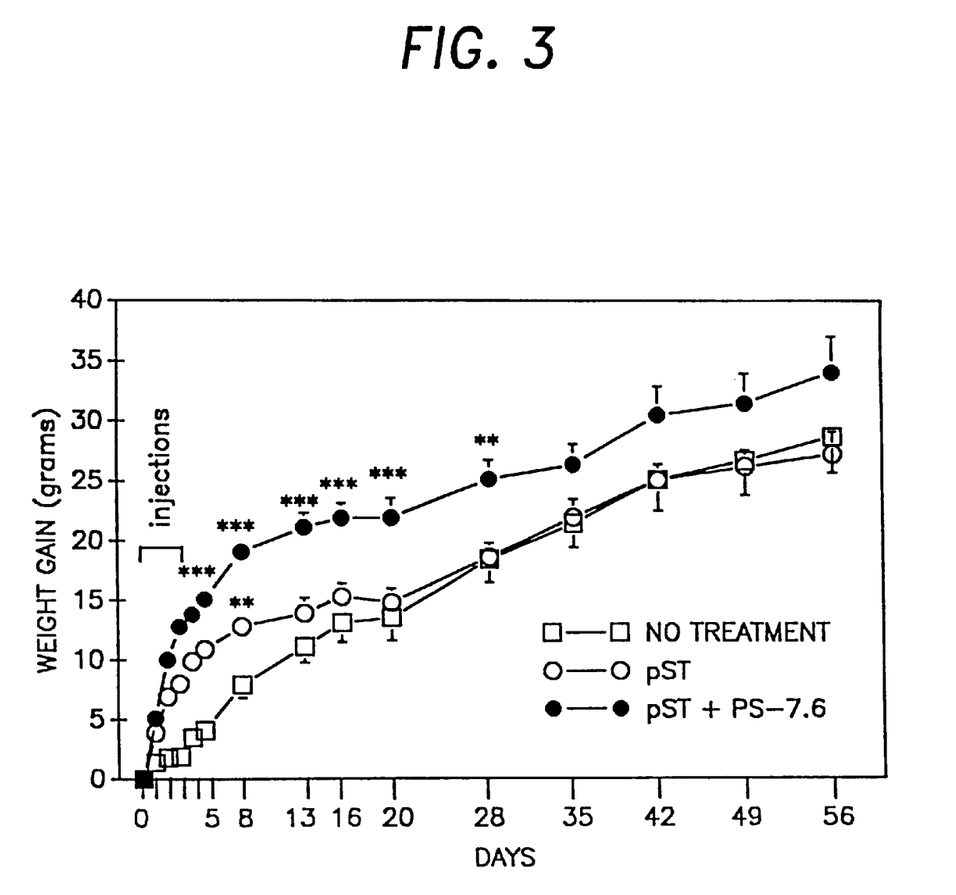
FIG. 3 depicts a long-term (56 days) time course study comparing the effect on the growth of hypophysectomized rats of treatment with pST alone, pST in combination with monoclonal antibody PS-7.6, or no treatment.
Figure 4:
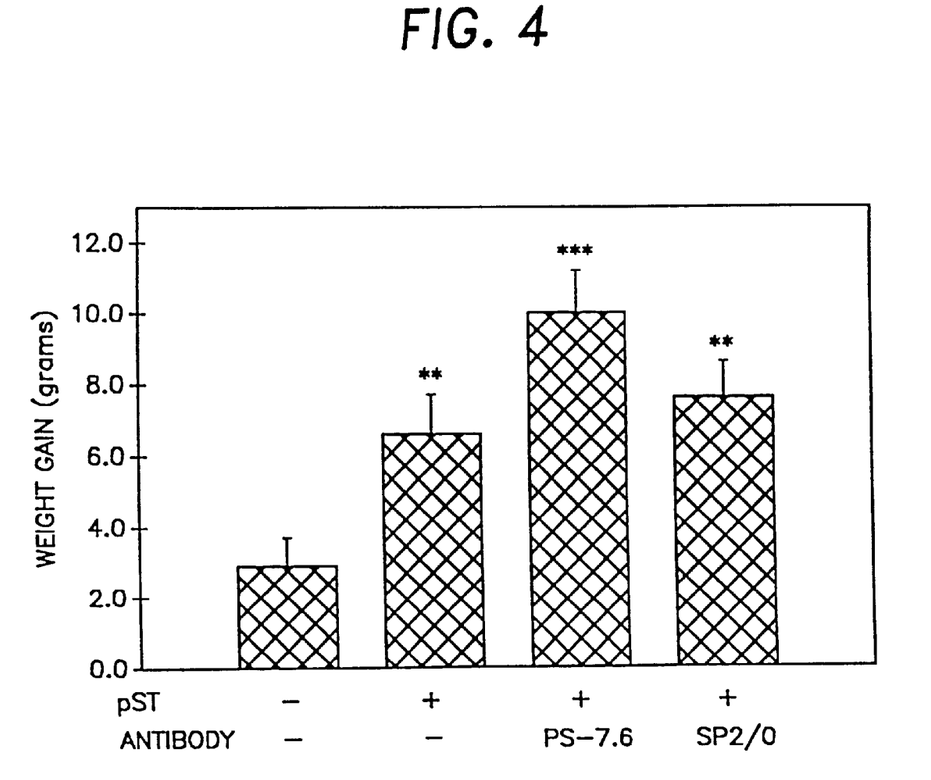
FIG. 4 depicts the effect on the growth of hypophysectomized rats treated with pST alone, pST in combination with control immunoglobulin from SP2/0 myeloma ascites, pST in combination with monoclonal antibody PS-7.6, or no treatment.
Figure 7:
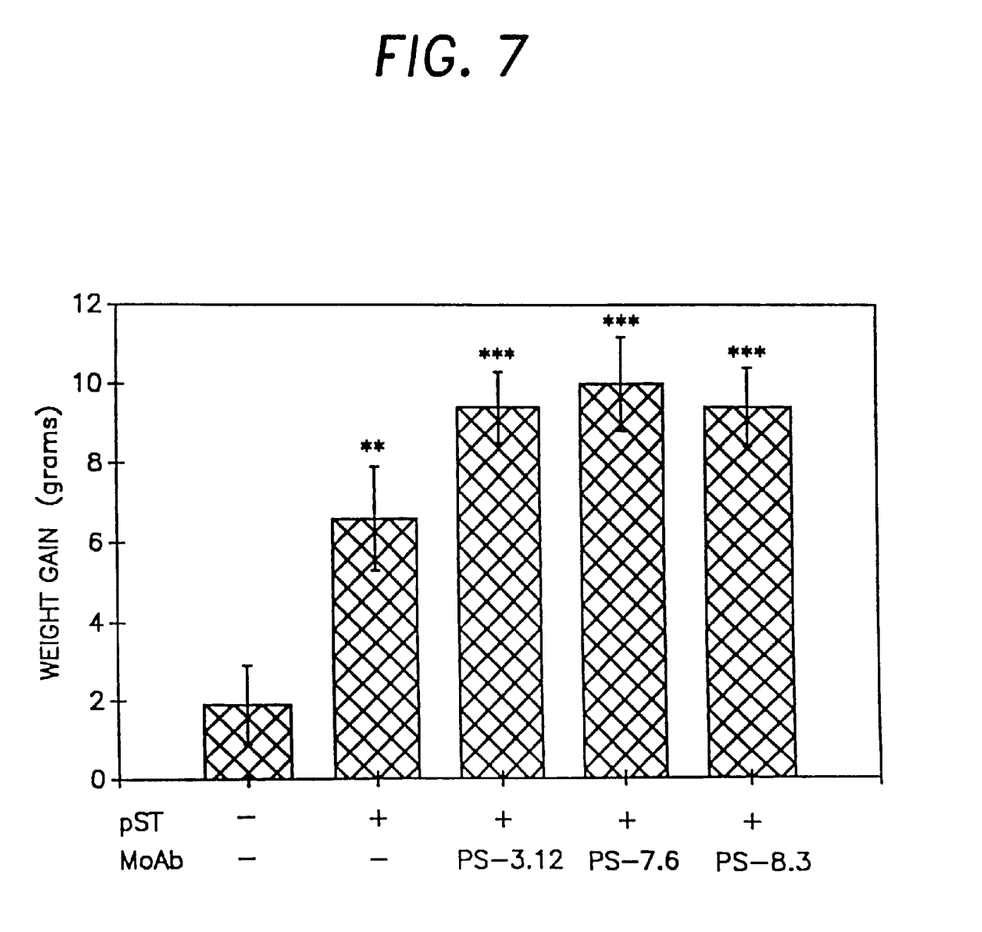
FIG. 7 depicts the effect on the growth of hypophysectomized rats treated with pST alone, pST in combination with monoclonal antibodies PS-3.12, PS-7.6 and PS-8.3, respectively, or no treatment.

The potentiation of activity of a somatotropin over prolonged periods of time by antibodies to said somatotropin is demonstrated using a similar hypox-rat assay. The growth of the animals is monitored for a longer period. The method is exemplified using pST and a monoclonal antibody to pST. Injections with pST alone for five days produce a noticeable weight gain in hypox-rats, but the effect is significant only up to eight days and completely coincides with the growth rate of untreated animals by day 28 (FIG. 3). However, treatment with monoclonal antibody PS-7.6 extends the elevated growth pattern at a significant level to 28 days. All antibody-treated animals remain noticeably heavier than pST-treated and untreated controls for at least 56 days after the initial treatment, clearly indicating its long persistency. The growth enhancement by antibody is extremely long-lasting, because a significant difference in weight gain between antibody-treated and control (pST alone) animals persists for at least 56 days after the initial treatment (FIG. 3). The growth potentiating effect of monoclonal antibody PS-7.6 on pST is significantly superior to that of a control polyclonal antibody. Monoclonal antibody PS-7.6 significantly heightens the effect of pST activity, whereas a control antibody (Ig) fails to affect pST activity after five days (FIG. 4). Monoclonal antibodies PS-3.12 and PS-8.3 are comparable to monoclonal antibody PS-7.6 in their pST growth potentiating effect (FIG. 7).

Figure 5:
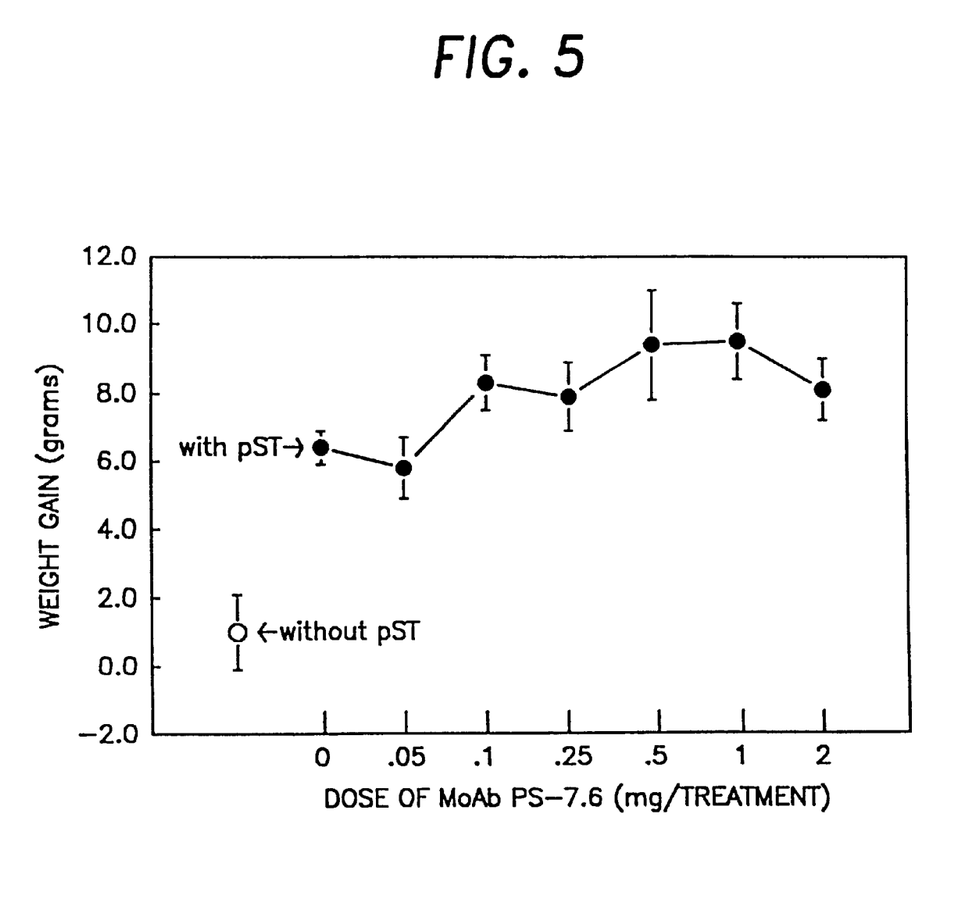
FIG. 5 depicts the dose response of the administration of monoclonal antibody PS-7.6 plus pST on the growth of hypophysectomized rats, in comparison with pST alone and no treatment (without pST).
Figure 6:
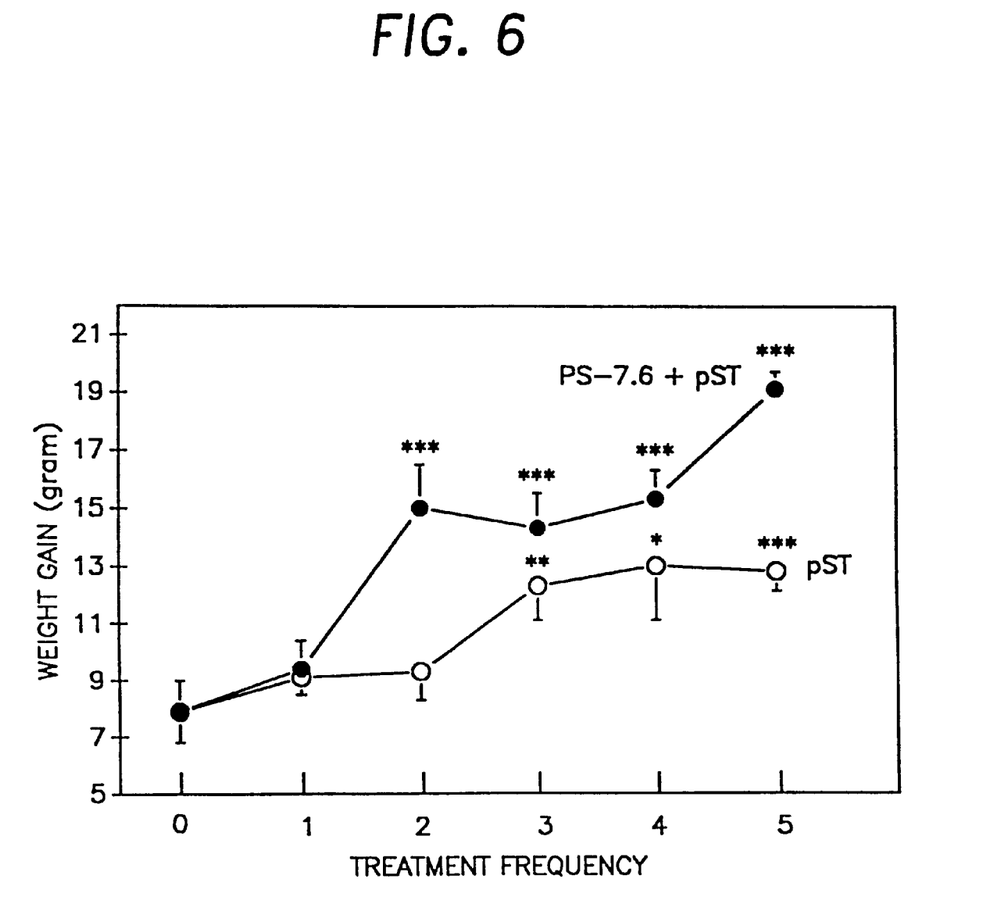
FIG. 6 depicts the effect of treatment frequency (one injection per day) with pST alone or pST in combination with monoclonal antibody PS-7.6 on the growth of hypophysectomized rats.

Although the effective dose of monoclonal antibody PS-7.6 ranges from 0.1 to 2.0 mg/injection, the optimal doses are 0.5 and 1.0 mg/injection (FIG. 5). The dose response results shown in FIG. 5 indicate that the action of monoclonal antibody PS-7.6 with pST is rapid. Repeated injections (five treatments) with monoclonal antibody PS-7.6 plus pST produces a maximum effect, but significant enhancement is detectable with as few as two treatments (FIG. 6). In contrast, a lesser enhancement with pST alone requires a minimum of three days of injections and a lesser enhancement is achieved with pST alone after five days of injections than with two days of injections with monoclonal antibody PS-7.6 plus pST (FIG. 6). The data in FIGS. 5 and 6 demonstrate that the monoclonal antibodies to pST of this invention (a) achieve an equivalent potentiation of pST while reducing the amount of pST administered, and (b) achieves an acceleration of the potentiation of pST.

Taken together, these data indicate that monoclonal antibodies PS-3.12, PS-7.6 are PS-8.3 are highly active in augmenting the somatogenesis of pST and, therefore, are useful in improving animal growth performance.

In order that this invention may be better understood, the following examples are set forth. The examples are for the purpose of illustration only and are not to be construed as limiting the scope of the invention.

EXAMPLE 1

1. Generation of Monoclonal Antibodies, Including Monoclonal Antibody PS-7.6

Balb/C mice, six to ten weeks of age, are purchased from Charles River Breeding Laboratories, Wilmington, Mass. These mice are immunized with 100 µg pST emulsified in complete Freund's adjuvant and boosted with 50 µg of pST every three weeks thereafter. Their spleens are removed three days after the last boosting and single cell suspensions of lymphocytes are prepared. These lymphocytes are fused with SP2/0 mouse myeloma cells lacking hypoxanthine phyosphoribosyl transferase (HPRT) with 50% polyethylene glycol, suspended in Dulbecco's modified Eagle medium (D-MEM) containing 20% fetal calf serum (Gibco), 0.175 µg/ml aminopterin, 13.6 µg/ml hypoxanthine, 3.88 µg/ml thymidine and 50 µg/ml gentamicin (HAT medium), and finally dispensed in 96-well culture plates. After being cultured for 10–14 days, supernatants of the hybridomas which survive due to the HPRT-positive phenotype of the lymphocytes (approximately 30%) are collected for antibody screening in a solid-phase ELISA. Those being determined to produce appropriate antibodies (by consistently achieving high titers in supernatants—approximately 25% of the approximately 30% referred to above, for a net of approximately 7%) are further subcloned by a limited dilution procedure to produce antibodies of interest.

Three hybridomas produce clones of particular interest. Samples of these hybridomas have been deposited on Apr. 12, 1990 with the American Type Culture Collection, 12301 Parklawn Drive, Rockville, Md. 20852 and have been assigned accession numbers on Apr. 17, 1990 as shown in Table 1, together with the designations of the monoclonal antibodies of interest produced by those hybridomas:

TABLE 1

| Hybridoma | Accession Number | Monoclonal Antibody |
| --- | --- | --- |
| PS-3.12 | ATCC HB 10415 | MoAb PS-3.12 |
| PS-7.6 | ATCC HB 10416 | MoAb PS-7.6 |
| PS-8.3 | ATCC HB 10417 | MoAb PS-8.3 |

The selected clones are injected intraperitoneally into Balb/C mice which are primed with pristane for the production of antibody-containing ascites. Identification of the isotype of the monoclonal antibodies is carried out with an antibody isotyping kit (Zymed Laboratories, South San Francisco, Calif.). The monoclonal antibody designated PS-7.6 is selected as exemplary for further study in this Example 1.

2. Preparation of Antibody

Ascites are collected from the peritoneal cavities of mice and Ig is purified with a 50% ammonium sulfate precipitation technique. Alternatively, samples are diluted to 50% with binding buffer (3M NaCl, 1.5M glycine, pH 8.9) and loaded onto a preparative Protein A Superose HR 16/5 column on a FPLC system (Pharmacia, Piscataway, N.J.). The non-Ig fraction is eluted from the column with the binding buffer and the bound Ig is subsequently collected by rinsing the column with 0.1M citric acid, pH 3. It is immediately neutralized to pH 7–8 with 2M Tris buffer, pH 8.2. Antibody prepared by both procedures is extensively dialyzed against phosphate-buffered saline (PBS), concentrated by ultrafiltration (Amicon, Danvers, Mass.), aliquoted, and finally stored at −20° C. until use.

3. Solid Phase ELISA

Antigens are dissolved in PBS and 1 µg in 100 µl is added to each well of a 96-well flat bottom polystyrene plate. After being incubated for one hour, the plate is washed three times with PBS containing 0.05% Tween-20 by an automatic plate washer (Dynatech Wash II, Chantilly, Va.). Each well is dispensed with 200 µl of 2% bovine serum albumin (Sigma)

and the plate is incubated for another hour. Test samples are added to the wells, incubated for 30 minutes, washed six times with PBS, and added with 100 μl of alkaline phosphatase-conjugated goat anti-mouse IgG F(ab')$_2$ (Zymed Laboratories, South San Francisco, Calif.). The plate is washed again after a 30 minute incubation and 100 μl of p-nitrophenyl phosphate (1 mg/ml, Sigma) in 0.1M diethanolamine, pH 10.3, is added as substrate for color development. Finally, the calorimetric response is recorded as optical density (OD) by an ELISA plate reader at a wavelength of 405 nm. The incubation procedure is always performed at 37° C.

4. Characterization of Monoclonal Antibody PS-7.6

Figure 1:
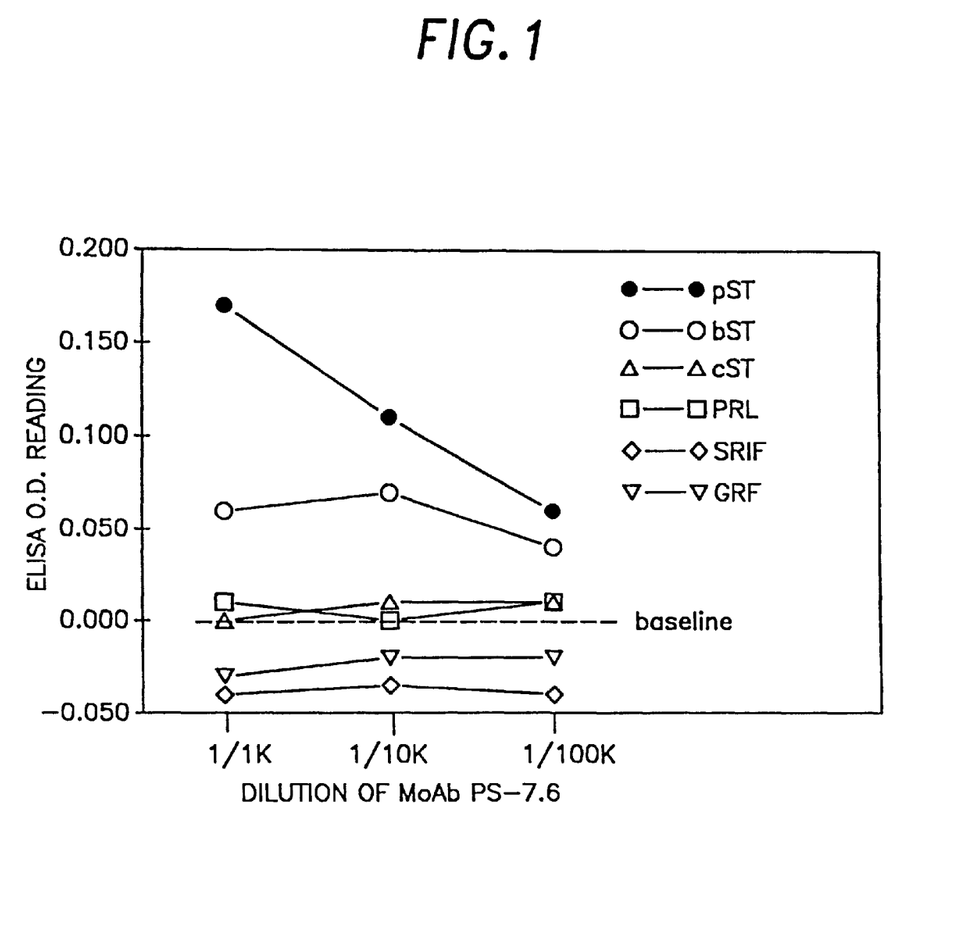
FIG. 1 depicts a study of the immunospecificity of monoclonal antibody PS-7.6 to various antigens, where pST, bST and cST are, respectively, porcine, bovine and chicken somatotropin, PRL is prolactin, SRIF is somatostatin and GRF is growth hormone releasing factor.

The immunospecificity of the PS-7.6 monoclonal antibody is tested in a solid phase ELISA. Various antigens are coated in the wells of a 96-well plate and a series of dilutions of monoclonal antibody PS-7.6 ascites is added for interaction. FIG. 1 indicates that monoclonal antibody PS-7.6 responds to pST antigen markedly well. It also indicates a slight cross-reactivity with bST, but not with cST, PRL, SRIF and GRF.

The isotype of monoclonal antibody PS-7.6 determined by an antigen-dependent, biotin-avidin amplified ELISA is IgG$_1$ with k light chain characteristics.

5. Biological Assays for pST and Antibody

The immunoreactivity of the monoclonal antibodies generated as described above is examined in conjunction with pST. Female Sprague-Dawley rats, 21 days of age and weighing 50–65 g, are obtained from the Taconic Farm, Germantown, N.Y. The bioassay is carried out with these hypox rats deficient in growth as a result of surgical removal of their pituitary glands. After delivery, these rats are kept for an additional 7–10 days of observation to ensure a complete hypophysectomy. Animals are randomly allocated to eight rats per group. Two groups of control animals are always included in all experiments. The first group consists of untreated hypox-rats which serve as negative controls. The other control group consists of hypox-rats which receive a minimal effective dose of pST (5 μg) by daily injection and thus serve as positive controls. Antibody (0.5 to 1 mg) mixed with 5 μg of PST at room temperature for one hour is administered subcutaneously to each experimental rat at the neck region. The growth of these animals is individually monitored and recorded as weight gain during the course of the experiment.

The results are presented as mean weight gain together with the standard error of means for each group of eight rats. The statistical evaluation is carried out by the least-squares analysis of variance for randomized design using the General Linear Models procedure of the Statistical Analysis System. Unless otherwise noted, the analysis is made by comparison with negative controls who received no treatment.

6. Growth Enhancement with Monoclonal Antibody PS-7.6

The growth-enhancing effect of monoclonal antibody PS-7.6 administered with pST is evaluated in hypox-rats. Hypox-rats are divided into four groups as described above. Daily injections of untreated control animals with 5 μg of pST for five days produce a significant weight gain as evidenced by an increase of the slope of their growth pattern. However, the effect is short-lived, because the accelerated growth curve of these control animals slows down as soon as the treatment of pST is terminated at day 5. Untreated controls show a retarded growth rate over a period of 16 days (FIG. 2). In contrast, the growth-promoting effect of pST is enhanced and extended over the 16 day period by monoclonal antibody PS-7.6 when both are incubated at room temperature for one hour prior to administration. Injections of monoclonal antibody PS-7.6 alone are ineffective.

In a separate experiment, an extremely long persistency of antibody effect (56 days) is demonstrated (FIG. 3). Animals receiving five daily injections of pST alone again show a significant increase in weight gain over untreated controls in the first eight days, but the overall growth after 56 days is identical to the untreated controls. Administration with a combination of pST and monoclonal antibody PS-7.6 not only further elevates the growth rate but also maintains these animals at a significantly heavier weight than either treated or untreated controls for as long as 28 days after the initial treatment ($p<0.01$). A noticeable difference in weight gain of this group of rats from both control groups persists for at least 56 days (25% over controls).

The pattern of administration of FIG. 3 is repeated with the inclusion of additional controls of non-specific Ig. The results after five days are presented in FIG. 4. Treatment with pST alone again markedly potentiates the growth of hypox-rats (weight gain=6.6 g) when compared with untreated controls (weight gain=2.9 g; $p<0.01$). Mixing pST with control Ig from SP2/0 myeloma ascites (American Type Culture Collection, Rockville, Md.) does not augment pST activity (weight gain=7.6 g; $p<0.5$), whereas mixing pST with monoclonal antibody PS-7.6 significantly heightens the effect (weight gain=10 g; $p<0.05$).

7. Dose Response Effect of Monoclonal Antibody PS-7.6 on the Enhancement of pST Activity A dose response study is carried out by treating hypox-rats with 5 μg per day of pST together with various doses of monoclonal antibody PS-7.6 for five consecutive days. The growth is scored at day 10. Untreated rats gain only 1 g over the entire course of the experiment. Data in FIG. 5 indicate that animals receiving pST alone produce a 6.4 g gain in weight. However, combination treatment with monoclonal antibody PS-7.6 significantly augments the pST effect over a dose range of 0.1–2 mg/treatment with the peak activity at 0.5 and 1 mg/treatment (weight gains=9.4 and 9.5 g, respectively).

8. Effect of Treatment Frequency of Monoclonal Antibody PS-7.6 on the Enhancement of pST Activity Hypox-rats are injected daily with 5 μg per day of pST or pST plus one mg monoclonal antibody PS-7.6 for one to five consecutive days and the growth is scored at day eight. The effect of pST alone is not evident until these rats receive three injections or more (FIG. 6). In contrast, a marked increase in weight gain by a combination treatment of pST and monoclonal antibody PS-7.6 is evident right after the second injection. A significant difference in weight gain is maintained between the two treatment groups after five injections; indeed the group receiving a combination of pST and monoclonal antibody PS-7.6 has a larger increase in weight gain after only two injections than that of the group receiving pST alone after five injections.

EXAMPLE 2

Steps 1–4 of Example 1 are repeated to generate, purify and characterize monoclonal antibodies PS-3.12 and PS-8.3. Growth enhancement with these antibodies is evaluated in hypox-rats in comparison with monoclonal antibody PS-7.6. Hypox-rats are divided into five groups in an adaptation of the procedure in step 5 of Example 1. The first group is untreated controls; the second group receives 5 μg of pST by injection for five days; the other groups receive 5 μg of pST for five days plus 1.0 mg of monoclonal antibodies PS-3.12, PS-7.6 and PS-8.3, respectively. The results after five days are presented in FIG. 7. Treatment with pST alone markedly potentiates the growth of hypox-rats (weight gain=6.6 g) when compared with untreated controls (weight gain=1.9 g); p<0.01. Treatment with pST together with each of the three monoclonal antibodies significantly heightens the effect (PS-3.12 weight gain=9.4 g; p<0.001; PS-7.6 weight gain= 10.0 g; p<0.001 g; PS-8.3 weight gain=9.4 g; p<0.001.

We claim:

1. A method for potentiating the activity of pST which comprises administering to a vertebrate, non-human an effective growth enhancing amount of pST and an effective pST-potentiating amount of one or more monoclonal antibodies which specifically bind pST or an antigenic equivalent of pST, wherein the monoclonal antibodies are selected from the group consisting of monoclonal antibodies designated PS-7.6 (ATCC HB 10416), PS-3.12 (ATCC HB 10415) and PS-8.3 (ATCC HB 10417).

2. The method of claim 1, wherein a monoclonal antibody used is that designated PS-7.6 (ATCC HB 10416).

3. The method of claim 1, wherein a monoclonal antibody used is that designated PS-3.12 (ATCC HB 10415).

4. The method of claim 1, wherein a monoclonal antibody used is that designated PS-8.3 PS-7.6 (ATCC HB 10416), PS-3.12 (ATCC HB 10415) and PS-8.3 (ATCC HB 10417).

5. The method of claim 1, wherein one or more monoclonal antibodies are administered together with pST.

6. The method of claim 1, wherein one or more monoclonal antibodies are administered prior to the administration of pST.

7. A method for achieving an equivalent potentiation of pST while reducing the amount of pST administered which comprises administering to a vertebrate, non-human an effective growth enhancing amount of pST and an effective pST-potentiating amount of one or more monoclonal antibodies which specifically bind pST or an antigenic equivalent of pST, wherein the monoclonal antibodies are selected from the group consisting of monoclonal antibodies designated PS-7.6, PS-3.12 and PS-8.3, such that an equivalent potentiation is achieved with said combination of pST and one or more monoclonal antibodies to pST as with a larger amount of pST administered alone.

8. The method of claim 7, wherein a monoclonal antibody used is that designated PS-7.6 (ATCC HB 10416).

9. The method of claim 7, wherein a monoclonal antibody used is that designated as PS-3.12 (ATCC HB 10415).

10. The method of claim 7, wherein a monoclonal antibody used is that designated PS-8.3 (ATCC HB 10417).

11. The method of claim 7, wherein one or more monoclonal antibodies are administered together with pST.

12. The method of claim 7, wherein one or more monoclonal antibodies are administered prior to the administration of pST.

13. A method for accelerating the potentiation of pST which comprises administering to a vertebrate, non-human an effective growth enhancing amount of pST and an effective pST-potentiating amount of one or more monoclonal antibodies which specifically bind pST or an antigenic equivalent of pST, wherein the monoclonal antibodies are selected from the group consisting of monoclonal antibodies designated PS-7.6 (ATCC HB 10416), PS-3.12 (ATCC HB 10415) and PS-8.3 (ATCC HB 10417) such that an equivalent potentiation is achieved with said combination of pST and one or more monoclonal antibodies to pST in less time than with pST administered alone.

14. The method of claim 13, wherein a monoclonal antibody used is that designated PS-7.6 (ATCC 10416).

15. The method of claim 13, wherein a monoclonal antibody used is that designated PS-3.12 (ATCC HB 10415).

16. The method of claim 13, wherein a monoclonal antibody used is that designated PS-8.3 (ATCC HB 10417).

17. The method of claim 13, wherein one or more monoclonal antibodies are administered together with pST.

18. The method of claim 13, wherein one or more monoclonal antibodies are administered prior to the administration of pST.

19. A method for potentiating the activity of a porcine somatotropin over prolonged periods of time which comprises administering to a vertebrate, non-human an effective growth enhancing amount of a porcine somatotropin and an effective porcine somatotropin-potentiating amount of one or more antibodies which specifically bind said porcine somatotropin or an antigenic equivalent of said porcine somatotropin, such that the weight of the vertebrate continues to exceed that of a vetebrate treated with the same amount of said porcine somatotopin alone over a given period of time wherein one or more of the antibodies are monoclonal antibodies selected from the group consisting of monoclonal antibodies designated PS-7.6 (ATCC HB 10416), PS-3.12 (ATCC HB 10415) and PS-8.3 (ATCC HB 10417).

20. The method of claim 19, wherein the monoclonal antibody is that designated PS-7.6 (ATCC HB 10416).

21. The method of claim 19, wherein the monoclonal antibody is that designated PS-3.12 (ATCC HB 10415).

22. The method of claim 19, wherein the monoclonal antibody is that designated PS-8.3 (ATCC HB 10417).

* * * * *